United States Patent [19]
Nickel et al.

[11] Patent Number: 5,360,923
[45] Date of Patent: Nov. 1, 1994

[54] PROCESS FOR SEPARATING OFF ALKANOLS, MIXTURES OF ALKANOLS AND WATER OR WATER ITSELF FROM OXYGEN-CONTAINING ORGANIC COMPOUNDS OF HIGHER CARBON NUMBER

[75] Inventors: Andreas Nickel, Wetter; Wolfgang Arlt, Berlin; Ingo Janisch, Kürten; Paul Wagner, Düsseldorf; Alexander Klausener, Cologne, all of Germany

[73] Assignee: Bayer Aktiengesellschaft, Leverkusen, Germany

[21] Appl. No.: 132,593

[22] Filed: Oct. 6, 1993

[30] Foreign Application Priority Data

Oct. 13, 1992 [DE] Germany .................. 4234525

[51] Int. Cl.$^5$ ............. C07C 27/26; C07C 29/76; C07C 69/96
[52] U.S. Cl. .................. 558/277; 568/913; 568/916
[58] Field of Search .............. 568/913 M; 558/277

[56] References Cited

U.S. PATENT DOCUMENTS

| | | |
|---|---|---|
| 3,657,113 | 4/1972 | Stancell et al. |
| 4,162,200 | 1/1979 | Himmele et al. |
| 4,798,674 | 1/1989 | Pasternak et al. ........ 568/913 M |
| 4,960,519 | 10/1990 | Pasternak et al. |
| 5,151,190 | 9/1992 | Seiryo . |
| 5,248,427 | 9/1993 | Spiske et al. |

FOREIGN PATENT DOCUMENTS

| | | |
|---|---|---|
| 0001780 | 5/1979 | European Pat. Off. |
| 0134055 | 3/1985 | European Pat. Off. |
| 0331846 | 9/1989 | European Pat. Off. |
| 0423949 | 4/1991 | European Pat. Off. |
| 0476370 | 3/1992 | European Pat. Off. |
| 2450856 | 4/1975 | Germany . |
| 2706684 | 8/1978 | Germany . |
| 2737265 | 3/1979 | Germany . |
| 2607003 | 8/1979 | Germany . |
| 3730065 | 9/1988 | Germany . |
| 1441356 | 6/1976 | United Kingdom . |
| 1470160 | 4/1977 | United Kingdom . |

OTHER PUBLICATIONS

Derwent Abstract of JP 02-212,456 1990.

Primary Examiner—Joseph E. Evans
Attorney, Agent, or Firm—Sprung, Horn, Kramer & Woods

[57] ABSTRACT

A first alkanol having 1 to 3 C atoms or a mixture of this first alkanol with water or water itself can be separated off from oxygen-containing organic compounds having 3 to 7 C atoms from the group comprising second alkanols and dialkyl carbonates, which always have at least 2 C atoms more than the first alkanol, by permeation on membranes if a membrane obtained by plasma polymerization is employed.

17 Claims, 3 Drawing Sheets

PROCESS FOR SEPARATING OFF ALKANOLS, MIXTURES OF ALKANOLS AND WATER OR WATER ITSELF FROM OXYGEN-CONTAINING ORGANIC COMPOUNDS OF HIGHER CARBON NUMBER

BACKGROUND OF THE INVENTION

Field of the Invention

The present invention relates to a process for separating off lower alkanols, mixtures of alkanols and water or water itself from oxygen-containing organic compounds from the group comprising higher alkanols and dialkyl carbonates. The separation is carried out by pervaporation or vapour permeation on a membrane which has been prepared by plasma polymerization.

The process according to the invention allows simplified separations, especially in those cases where distillative separation processes fail because of the presence of an azeotrope. This is of importance for many mixtures of various alkanols, in particular those also containing water, and for separation of dialkyl carbonates from the alcohols on which they are based, again also in those cases where a content of water is present, and for the separation of dialkyl carbonate from water itself. A very important industrial problem of this type is the separation of methanol from dimethyl carbonate, if appropriate in the presence of water contained in the mixture. Another important industrial problem of this type is the separation of water from dimethyl carbonate.

Description of the Related Art

Separation of the mixtures described was hitherto carried out, for example, by two-pressure distillation (compare DE-A 2 607 003 and JP 02-212 456), since it is known that the composition of azeotropic mixtures is pressure-dependent. The separation quota obtained by this procedure is frequently inadequate and must be supplemented by other physical processes, for example by crystallization. Furthermore, pressure apparatuses always result in higher investment costs; because the temperature level is increased by the pressure, increased formation of by-products is also always to be expected.

In addition to distillation under increased pressure, attempts have also been made to separate mixtures of the type described by extractive distillation. In the case of separation of the dimethyl carbonate/methanol azeotrope, water is preferably used as the extraction agent here (compare DE-A 2 450 856). The ratio of water to dimethyl carbonate required is 20:1. This large amount of water must be separated from the methanol again in a further distillation column. It is an additional disadvantage here that water has more than 4 times the heat of evaporation and more than twice the thermal capacity of organic compounds; both properties lead to an increased energy consumption.

An improvement in extractive distillation by using organic solvents as additives also similarly has disadvantages due to the need to work up and recycle these additives (compare EP-A 00 1780; DE-A 2 706 684 and DE-A 2 737 265).

There have therefore already been attempts to separate, with the aid of membrane technology, mixtures which are difficult to separate. EP 331 846 thus describes the separation of short-chain alcohols from oxygen-containing organic compounds, such as ethers, aldehydes, ketones or esters, with the aid of a multi layer membrane. The separating membrane in this arrangement comprises either a polyvinyl alcohol layer crosslinked with aliphatic polyaldehydes or a resin which is also employed in ion exchangers and contains acid groups which have been modified by quaternary ammonium salts. A polyester woven fabric is used as the carrier material for the multilayer membrane; a porous support membrane which is furthermore used comprises a polysulphone woven fabric. This membrane is of relatively complicated structure. Because of its chemical composition, the operating temperature is limited to 77° C. and results in a low maximum flow rate here of 1.5 kg/m$^2$×h. This imposes limits on industrial use. The permeate concentrations described for methanol of from 73% to only 93% in the case of separation of dimethyl carbonate and methanol mean that the methanol obtained by this procedure must be freed from the residual 7% of dimethyl carbonate in a further operation.

According to the description in EP423 949, an attempt is made to overcome the disadvantages described for the process according to EP 331 846 by another membrane which is a blend of polyvinyl alcohol and polyacrylic acid on polyacrylonitrile as the support membrane. In the case of separation of dimethyl carbonate from methanol, a concentration of methanol of from 73% to about 95% is achieved at a flow rate of about 2 kg/m$^2$×h; this concentration represents, on the part of the retained material, the minimum requirement for purified dimethyl carbonate for use in further processes.

According to the description of EP 476 370, a membrane which is obtained by plasma polymerization and is preferably a composite membrane is employed for separating off the water of reaction from an esterification mixture. An esterification mixture according to this description comprises unreacted carboxylic acid, unreacted alcohol, the ester desired as the reaction product, the water of reaction formed during the reaction and an acid esterification catalyst. The separation of the water of reaction on the membrane is then followed by separation elsewhere of the retained material into the ester product stream and into the acids and alcohols which have not yet reacted and are to be recycled. The process of EP 476 370 is accordingly characterized in that, apart from the water, no substantial organic constituents pass through the membrane; it is particularly important here that the esterifying alcohol does not pass through the membrane.

Plasma polymerization for modification of surfaces, for example of membranes, is already known, for example from Houben-Weyl, Methoden der organischen Chemie (Methods of Organic Chemistry), Volume VI/5b, part II (1975, pages 1,563 to 1,591).

SUMMARY OF THE INVENTION

A process has been found for separating off a first alkanol having 1 to 3 C atoms, or a mixture of this first alcohol with water, or water itself, from oxygen-containing organic compounds having 3 to 7 C atoms form the group comprising a second alkanol and alkyl carbonates, the first alkanol always having at least 2 C atoms, preferably exactly 2 C atoms, less than each of the oxygen-containing organic compounds, by pervaporation or vapour permeation, which is characterized in that the mixture described is fed at 40° to 130° C., preferably 40° to 100° C., to a membrane which has been obtained by plasma polymerization, a pressure of 0.5 to 10 bar, preferably 0.8 to 6 bar, particularly preferably 1 to 5 bar, being established on the feed side and a pressure of not more than 100 mbar, preferably not more than 20 mbar, being established on the permeate side and the first alkanol or the mixture of first alkanol and water, or water itself in concentrated from being obtained as the permeate and the oxygen-containing organic compound in concentrated form being obtained as the retained material.

BRIEF DESCRIPTION OF THE DRAWINGS

The accompanying drawings show exemplary permeate flow rates and permeate concentrations (FIGS. 1 and 2), and exemplary compositions of retained material and permeate (FIGS. 3 and 4) as are obtained in working Examples 2 and 3.

DETAILED DESCRIPTION OF THE INVENTION

Figure 1:
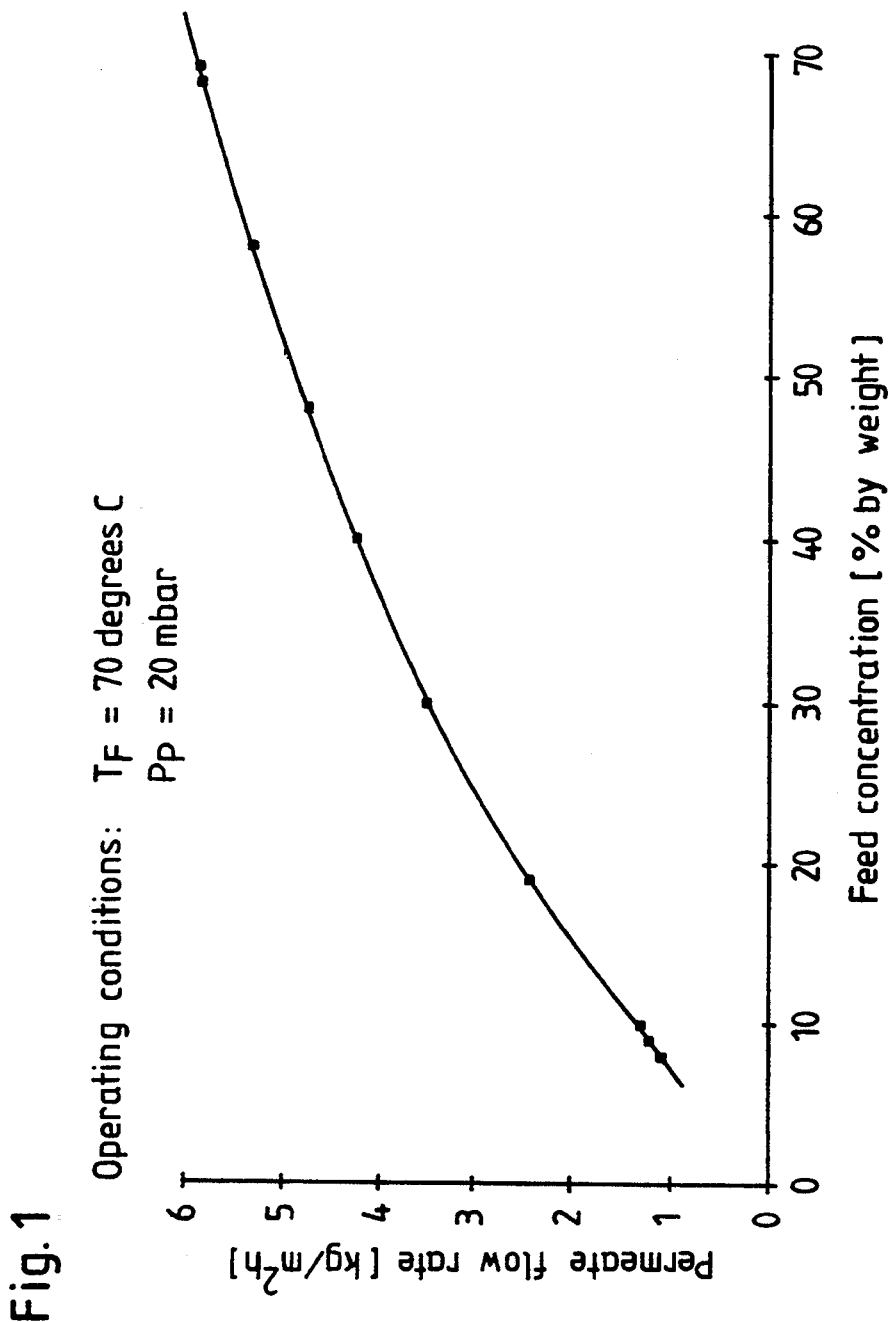

The retained alkyl carbonates are preferably symmetric.

The process according to the invention is accordingly suitable, for example, for the following separation tasks: the removal of methanol or methanol/water or water from a mixture with the alkanols which are higher by 2 C atoms, such as propanol, isopropanol, butanol, isobutanol, tert-butanol and the isomeric pentanols, hexanols and heptanols; the removal of ethanol or ethanol/water or water from butanol, isobutanol, tert-butanol and the isomeric pentanols, hexanols and heptanols; the removal of propanol or isopropanol or mixtures thereof with water from the isomeric pentanols, hexanols and heptanols; the removal of methanol or methanol/water or water from dimethyl carbonate; the removal of ethanol or ethanol/water or water from diethyl carbonate; and the removal of propanol or isopropanol or mixtures thereof with $H_2O$ or water from dipropyl carbonate or diisopropyl carbonate respectively.

Under the separation tasks mentioned which are to be accomplished by the process according to the invention, removal of the first alkanol or its mixture with water or water from the associated dialkyl carbonate is particularly important. The task of removal of methanol or methanol/$H_2O$ or water itself from the mixture with dimethyl carbonate (DMC) is especially important.

The process according to the invention is carried out at a feed temperature of 40° to 130° C., preferably 40° to 100° C. A pressure of 0.5 to 10 bar, preferably 0.8 to 6 bar, particularly preferably 1 to 5 bar, is established on the feed side. A pressure of not more than 100 mbar, preferably not more than 20 mbar, for example 1 to 100 mbar, preferably 1 to 20 mbar, is established on a permeate side.

In carrying out the process according to the invention as pervaporation, the feed mixture is brought up to the membrane in liquid form and the pressure and temperature on the feed side are established such that the pressure is above the boiling pressure of the feed mixture.

However, it is also possible to carry out the process according to the invention in the form of vapour permeation, the feed mixture being brought to the membrane in vapour form or in the form of a liquid in the boiling state, preferably in vapour form. In this case, the pressures and temperatures are chosen and combined within the ranges stated such that the pressure, as a function of the temperature, is not more than the vapour pressure of the feed mixture, and is preferably below it. If appropriate, in the case of vapour permeation, the feed mixture in vapour form can be brought up to the membrane with the aid of a stream of carrier gas comprising an inert gas or a mixture of several inert gases. Inert gases which can be used are, for example, nitrogen, the noble gases, lower hydrocarbons, air, carbon monoxide or carbon dioxide.

The permeate is initially obtained in vapour form and can be removed from the membrane in this form or can first be condensed and removed from the permeate space as a condensate. In the case of gaseous removal, an inert carrier gas of the type described above can also be employed here.

The set-up of an apparatus for carrying out the process according to the invention is simple and comprises a reservoir tank for the mixture to be separated, a pump for establishing the desired feed pressure, a module with the membrane which is to be employed according to the invention and is obtainable by plasma polymerization, a means of removing the retained material which remains on the in-flow side of the membrane and a possibility for removing the permeate, the latter possibility being characterized, above all, by the vacuum pump required for maintaining the reduced pressure. The permeate side can have a condenser before or after the vacuum pump.

It is furthermore possible for the process according to the invention to be operated as it were batchwise by treatment of a predetermined amount of mixture, or to be operated in a completely continuous manner. In the case of batchwise procedure, it is furthermore possible for the retained material to be recycled to the storage tank for the mixture to be separated and in this way for the amount of mixture to be brought repeatedly to the membrane until a desired separation effect is achieved. In the case of a continuous procedure, it is furthermore possible for the retained material to be brought to a further module and for multistage treatment thus to be carried out until the desired separation effect is achieved.

Membranes which are to be employed according to the invention and are obtained by plasma polymerization are distinguished by a dense, pore-free structure. For their preparation, activated molecules of various organic compounds, or fragments thereof, are produced from these organic compounds by the action of a plasma in vacuo and are precipitated on an opposite electrode and polymerized there as the reactive state reacts. Glow discharges are often used to form the plasma. The range of $10^{-3}$ to 20 mbar is often used as the vacuum. Because of this preparation procedure, no recurring monomer units are to be found in the plasma polymers, but rather a three-dimensional network of different atoms and atomic groups is formed.

For mechanically safe handling of the membranes formed by plasma polymerization, these are in general applied to a porous carrier material. This can be a woven fabric or a non-woven of various, preferably heat-resistant polymer. In a further embodiment, instead of such a carrier material or in addition to a carrier material, an asymmetric porous first membrane can be employed, onto the which the pore-free, dense membrane prepared by plasma polymerization is deposited in the form of a composite membrane. Asymmetric porous first membranes of this type are prepared, for example, by the phase inversion technique known to the expert. The asymmetric membrane is arranged such that the side having the larger pores forms the reverse side, which is also closed off, if appropriate, by a woven fabric or non-woven of the type mentioned, and that the side having the finer pores is facing the plasma coating. Polyacrylonitrile is often employed as the material for such an asymmetric porous membrane.

The organic compounds which are activated in the plasma can belong to very diverse substance classes. Examples which may be mentioned are: saturated or unsaturated aliphatic hydrocarbons, such as methane, ethane, propane, butanes, hexanes, ethylene, propylene, butylene, butadiene and acetylene; halogenohydrocarbons based on the aliphatic compounds mentioned and having chlorine, bromine and/or fluorine atoms; aromatic hydrocarbons, such as benzene, toluene, xylene and ethylbenzene; and monomers which are capable of polymerization, in addition to the abovementioned unsaturated hydrocarbons, such as acrylonitrile, vinyl chloride, acrylic acid esters, styrene and others. It has also already been described (DE-OS 3 730 065) that fragments in activated form can be extracted from compact polymer bodies in the plasma and can be polymerized again on a counter-electrode or on a support layer attached thereto, with simultaneous deactivation. In this case also, a dense pore-free membrane prepared by plasma polymerization is obtained.

Membranes of plasma polymers for separation purposes are, for example, those according to U.S. Pat. No. 3,657,113. the plasma polymer described therein is applied under a pressure of 0.1–5 mm Hg and in a thickness of 0.03 to 2 μm to a layer of an amorphous polymer. Polyphenylene oxide and siloxanes and their copolymers are mentioned as preferred amorphous polymers. Aromatic compounds, nitriles and polyunsaturated compounds are preferred as the plasma gas. A composite membrane having a pore-free separating layer furthermore is known from EP-A 0 134 055, the pore-free, selective separating layer being applied in a thickness of less than 0.1 μm to a dense polymer layer of a conventional polymer. The layer of the conventional polymer is between 0.01 and 5 μm thick, preferably comprises polydimethylsiloxane, and is carried by a porous sub-structure. The selective separating layer formed by plasma polymerization is silicone-free, but can in turn also carry, on the side facing the mixture to be separated, a thin protective layer which preferably comprises the same material as the polymer layer onto which the plasma layer is applied, for example silicone.

In the case of the membranes prepared by plasma polymerization which are preferably to be employed, deposition of the plasma polymers which form the selective separating layer is carried out in an apparatus which comprises a tank which has pressure regulation and regulatable gas inlet systems and can be evacuated and devices for measurement of the overall pressure and the partial pressures of the gas components. Two electrodes opposite to one another, one of which is earthed, are in the tank. The porous substrate onto which the plasma polymer layer is deposited is to be found on one electrode. An electrical alternating field with frequencies of 10 kHz to 20 GHz and a regulatable electrical output of the alternating field lies between the two electrodes. In a preferred embodiment, a web of the porous substrate is drawn at a controlled speed over one electrode so that continuous deposition of a plasma polymer layer takes place. It has been found, surprisingly, the pore-free, dense plasma polymer layers can be deposited directly on a porous substrate without a dense intermediate layer first having to be applied between the porous substrate and plasma polymer layer. Porous materials of carbon, metal, ceramic or polymers can be used as substrates by this procedure, substrates in the form of porous membranes having an asymmetric pore structure, for example of polyacrylonitrile, polysulphone or other polymers, preferably being used.

It is important here that these substrates have pores having a diameter of less than 100 nm on the surface on which the plasma polymer layer is deposited. Larger pores can no longer be bridged reliably with the plasma polymer layer, so that defects arise. The pores preferably have a pore size which is as uniform as possible, with an average pore width of 5 to 40 nm. Porous membranes having an asymmetric pore structure are known per se and are widely used, for example, for ultrafiltration. They are usually 30 to 150 μm thick. The commercially obtainable membranes additionally have a carrier of a non-woven or a woven fabric and then have a total thickness of 100 to 300 μm.

The gas mixture in the glow discharge region between the electrodes, from which the plasma polymer is formed, comprises at least one matrix-forming component and at least one component which is not matrix-forming, and furthermore an oxygen-containing component.

All hydrocarbons which have a vapour pressure of at least 0.5 mbar at 50° C. can be used as the matrix-forming component. Examples of suitable hydrocarbons are aliphatic hydrocarbons having 1 to 12 C atoms, such as methane, butane or decane, or aromatic hydrocarbons, such as benzene or toluene. Low molecular weight hydrocarbons having at least one C—C double bond are preferred, ethene and propene being particularly preferred.

Components which are not matrix-forming are inorganic compounds which contain nitrogen, silicon, sulphur or phosphorus and have a vapour pressure of at least 1 mbar at 50° C. Examples of suitable compounds are hydrogen compounds, such as ammonia, silanes, hydrogen sulphide or phosphines, or oxides of nitrogen, sulphur or phosphorus, for example laughing gas, sulphur dioxide or sulphur trioxide. Nitrogen-containing compounds, such as ammonia, hydrazine or nitrogen, are preferred, ammonia being particularly preferred.

Suitable oxygen-containing components are oxygen, carbon dioxide, carbon monoxide and water. Oxygen, carbon dioxide and water re preferred.

The matrix-forming components and components which are not matrix-forming are in general employed in a molar ratio of 0.2 to 5, preferably 0.5 to 1.5.

The oxygen-containing component is in general used in a molar ratio, based on the sum of matrix-forming component and component which is not matrix-forming, of 0.05 to 0.3, preferably 0.1 to 0.2. The pressure in the plasma reactor is in general $10^{-3}$ to 10 mbar, preferably 0.1 to 1 mbar. The electrical field in general operates in the range from 10 kHz to 5 GHz, preferably 20 kHz to 14 MHz. The system is in general operated with an electrical output of 0.01 to 3 watt per $cm^2$ electrode area, preferably 0.1 to 1 watt per $cm^2$. The deposition time is in general 2 seconds to 1 hour, preferably 20 seconds to 10 minutes. The thickness of the plasma polymer layer deposited is in general 0.1 to 2 μm, preferably 0.5 to 1 μm.

It is astonishing that a membrane prepared by plasma polymerization, for which it was to be assumed, on the basis of the description disclosed to date, that lower alcohols also remain on the retained material side, can be employed successfully for the stated separation problem.

EXAMPLES

Example 1

During pervaporative removal of methanol from a dimethyl carbonate/methanol mixture, the following experimental values were obtained at a feed temperature of 50° C., a pressure of 3 bar on the feed side and a permeate pressure of 20 mbar using membrane sample No. 270 from GFT, Neunkirchen- Heinitz (DE) (Table 1):

TABLE 1

| Feed concentration % by weight of methanol | Permeate flow rate kg/m$^2$ × hour | Permeate concentration % by weight of methanol |
|---|---|---|
| 10 | 0.5 | 92 |
| 20 | 0.75 | 93.5 |
| 30 | 1.1 | 95.5 |
| 40 | 1.4 | 96.5 |
| 50 | 1.65 | 97 |
| 60 | 1.9 | 98 |
| 70 | 2.1 | 98 |

Approximately twice the permeate flow rates were obtained at a feed temperature of 70° C.

Example 2

Figure 2:
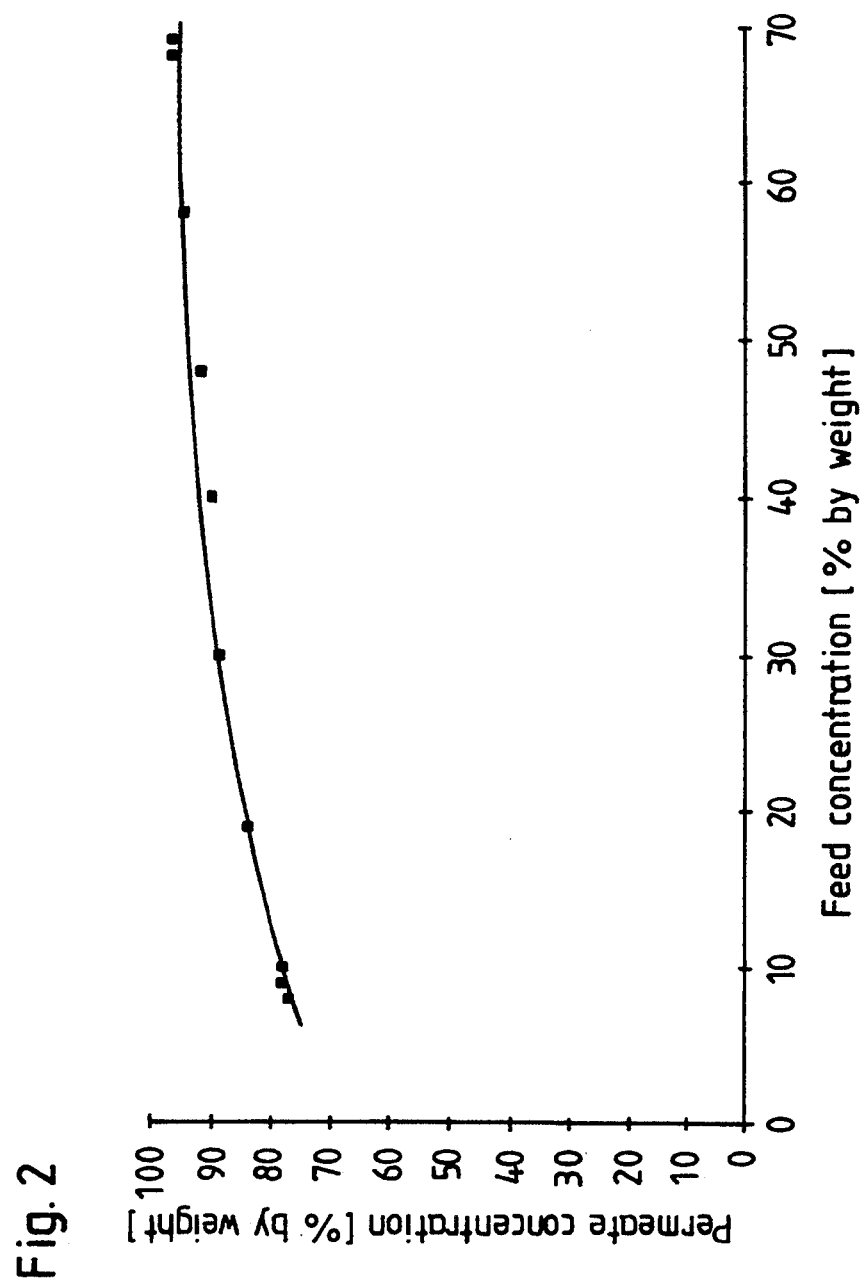

The permeate flow rates and permeate concentration shown in the attached FIG. 1 and FIG. 2 were obtained, as a function of the feed concentration, at a feed temperature of 70° C. and a permeate pressure of 20 mbar using membrane sample No. 300 in a manner analogous to Example 1 (dimethyl carbonate/methanol system).

Example 3

Figure 3:
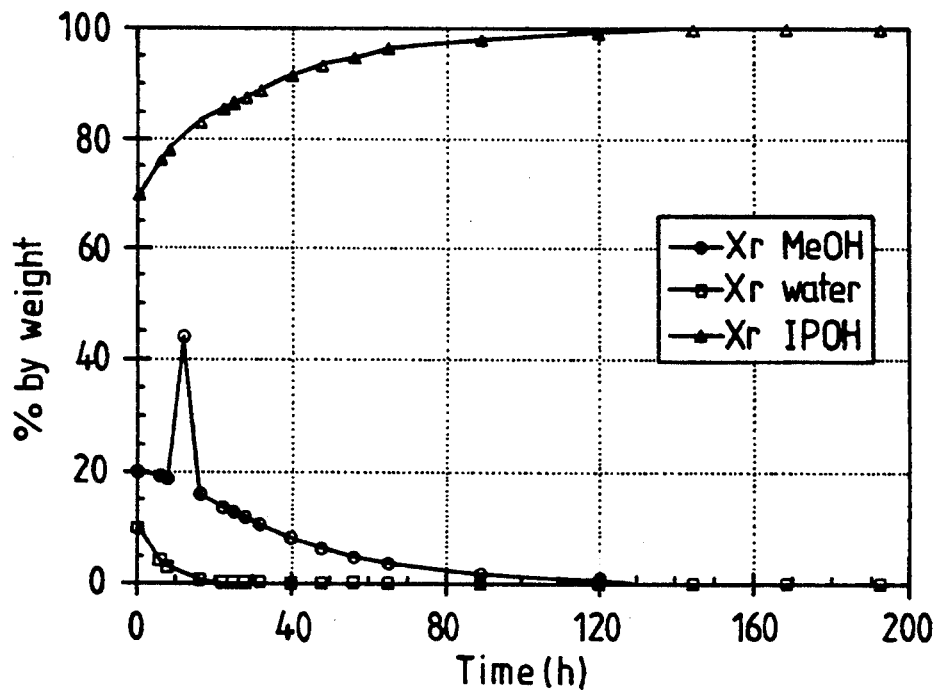
Figure 4:
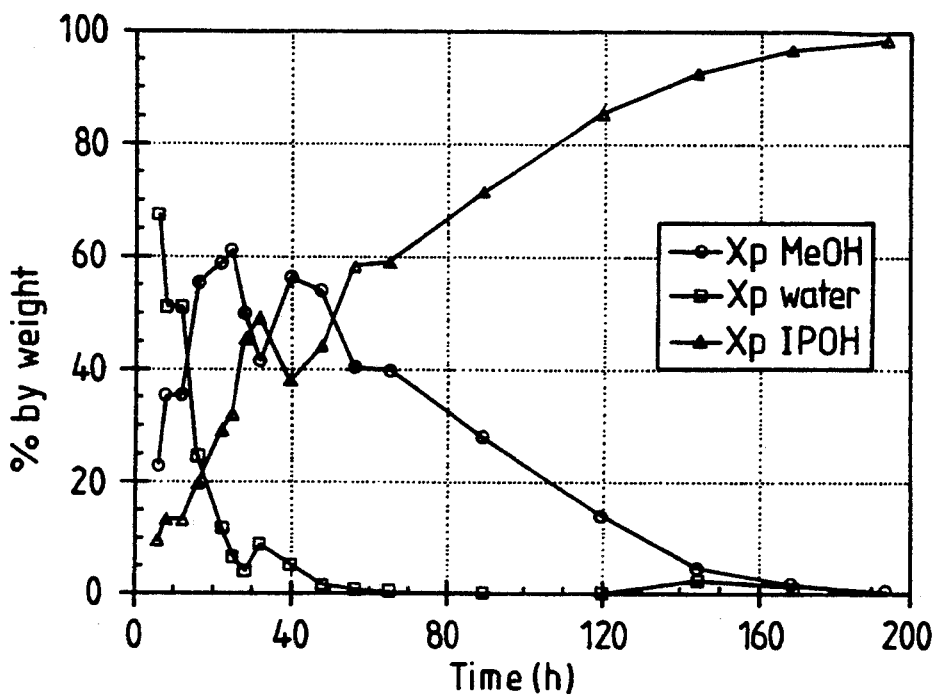

A feed mixture having a composition of 70% by weight of i-propyl alcohol (IPOH), 20% by weight of methanol (MeOH) and 10% by weight of water (H$_2$O) was treated on a membrane sample No. 229 at a feed temperature of 70° C. and a permeate pressure of 10 mbar such that the permeate was removed from the system but the retained material was recycled continuously as the feed. The compositions of retained material (Xr) and permeate (Xp) shown in the attached FIG. 3 and FIG. 4 respectively were obtained as a function of time (hours).

Example 4

In the pervaporative removal of water from a dimethyl carbonate/water mixture using a membrane sample No. 300 from GFT, Neunkirchen-Heinitz (DE), the following results were obtained:

At a content of water in the feed mixture of 2.7% by weight (remainder dimethyl carbonate) a permeate flow rate of 0.8 kg/m$^2$×h and a permeate concentration of 94.7% by weight of water were found.

Example 5 (Preparation of Membranes which can be Employed According to the Invention; Percentage Data are in % by Weight)

a) A porous membrane of polyacrylonitrile having an asymmetric pore structure was applied to one of the electrodes in a vessel which could be evacuated and was provided with a pressure regulation, regulatable feeds for gaseous and vaporous matrix-forming components, components which are not matrix-forming and oxygen-containing components and contained two electrodes opposite to one another, between which an electrical alternating field can be applied. The membrane has pores having an average pore diameter of 20 nm on the "fine side". The vessel was evacuated to a total pressure of 10$^{-4}$ mbar. Ethylene was let in at a rate of 1.34 mmol/minute as the matrix-forming gas and ammonia was let in at 1.65 mmol/minute as the gas which is not matrix-forming. The total pressure was kept at 0.4 mbar. An electrical discharge having a frequency of 37 kilohertz was activated between the electrodes, each of which had an area of 630 cm$^2$, the system being operated at an output of 500 watt. After a deposition time of 5 minutes, the gas feed and electrical alternating field were switched off, the reactor was flooded with air and the membrane was removed.

b) a plasma polymer membrane was prepared as described under a). The gas flow rates of the matrix-forming components and the components which are not matrix-forming were unchanged, as was the total pressure. Oxygen was additionally let in at a rate of 0.38 mmol/minute; at a frequency of 37 kHz, the electrical output was 215 W and the treatment time was 5 minutes. A separating layer having a thickness of 0.5 µm was obtained.

c) A membrane was prepared as under a); ethene at 1.27 mmol/minutes served as the matrix-forming gas and ammonia at 1.7 mmol/minute served as the gas which is not matrix-forming. Carbon dioxide furthermore was added at a rate of 0.22 mmol/minute and the total pressure was adjusted to 0.8 mbar. 500 W was maintained at 37 kHz for 3 minutes. The resulting membrane had a separating layer having a thickness of 0.6 µm.

d) A membrane was prepared as under a); an assymetric polysulphone ultrafiltration membrane which had pores having an average pore diameter of 30 nm on the fine side served as the substrate. Ethene was let in at 1.34 mmol/minute, nitrogen was let in as the component which is not matrix-forming at 0.8 mmol/minute, and water was furthermore let in at 0.25 mmol/minute. A membrane having a separating layer thickness of 0.5 µm was obtained at a total pressure of 0.8 mbar and an output of 425 W at 37 kHz over a period of 5 minutes.

e) A plasma polymer layer was deposited onto a porous asymmetric polyacrylonitrile ultrafiltration membrane having an average pore radius on the fine side of 14 nm as under a). Propene was metered in as the matrix-forming gas at 1.3 mmol/minute, ammonia was metered in as the component which is not matrix-forming at 1.6 mmol/minute and 0.4 mmol/minute of oxygen was furthermore metered in. The treatment was carried out at a total pressure of 0.8 mbar with 35 kHz at 215 W for 5 minutes. A membrane having a separating layer 0.5 µm thick was obtained by this procedure.

What is claimed is:

1. A process for separating off a first alkanol having 1 to 3 C atoms, or a mixture of this first alkanol with water from oxygen-containing organic compounds having 3 to 7 C atoms from the group comprising a second alkanol and dialkyl carbonates, the first alkanol always having at least 2 C atoms less than each of the oxygen-containing organic compounds, by pervaporation or vapour permeation, wherein the mixture described is fed at 40° to 130° C., to a membrane which has been obtained by plasma polymerization, a pressure of 0.5 to 10 bar being established on the feed side and a pressure of not more than 100 mbar being established on the permeate side and the first alkanol or the mixture of first alkanol and water in concentrated form being obtained as the permeate and the oxygen-containing organic compound in concentrated form being obtained as the retained material.

2. The process of claim 1, wherein the first alkanol has exactly 2 carbon atoms less than the oxygen-containing compounds.

3. The process of claim 1, wherein the mixture described is fed at 40° to 100° C.

4. The process of claim 1, wherein a pressure of 0.8 to 6 bar is established on the feed side.

5. The process of claim 4, wherein a pressure of 1 to 5 is established on the feed side.

6. The process of claim 1, wherein a pressure of not more than 20 mbar is established on the permeate side.

7. The process of claim 1, wherein the first alkanol or its mixture with water is separated off from symmetric dialkyl carbonates having 3 to 7 atoms, the first alkanol being the ester-alcohol of the carbonate.

8. The process of claim 1, wherein methanol or a methanol/water mixture is separated off from dimethyl carbonate.

9. The process of claim 1, wherein, when carried out as pervaporation, the feed pressure is established as a function of the temperature such that it is above the boiling pressure of the feed.

10. The process of claim 1, wherein, when carried out as vapour permeation, the feed pressure is established as a function of the temperature such that it is not more than the vapour pressure of the feed.

11. The process of claim 10, wherein the feed pressure is established below the vapour pressure of the feed.

12. The process of claim 1, wherein a composite membrane which comprises a carrier material and a pore-free layer applied thereto by plasma polymerization is employed.

13. The process of claim 12, wherein the carrier material is a porous polymer.

14. The process of claim 13, wherein the carrier material is a porous asymmetric polymer which has on its fine side pores having an average pore diameter of less that 100 nm.

15. The process of claim 12, wherein the carrier material is built up on the basis of acrylonitrile.

16. The process of claim 13, wherein the composite membrane on the porous carrier material is prepared by plasma polymerization of one or more hydrocarbons as the matrix-forming component and one or more nitrogen-, silicon-, sulphur- or phosphorus-containing inorganic compounds as the component which is not matrix-forming, with the aid of a glow discharge in an electrical alternating field, the preparation being carried out in the absence or presence of an oxygen-containing compound.

17. The process of claim 16, wherein ethene or propene is employed as the matrix-forming component, ammonia or nitrogen is employed as the component which is not matrix-forming an oxygen, carbon dioxide or water is employed as the oxygen-containing compound.

* * * * *

UNITED STATES PATENT AND TRADEMARK OFFICE
CERTIFICATE OF CORRECTION

PATENT NO. : 5,360,923
DATED : November 1, 1994
INVENTOR(S) : Nickel, et al.

It is certified that error appears in the above-indentified patent and that said Letters Patent is hereby corrected as shown below:

Column 9, line 14,        after "5" insert --bar--

Column 9, line 22,        delete "claim 1" and substitute --claim 7--

Signed and Sealed this

Fifteenth Day of December, 1998

Attest:

BRUCE LEHMAN

*Attesting Officer*      *Commissioner of Patents and Trademarks*